United States Patent [19]

Brumm et al.

[11] Patent Number: 4,814,273

[45] Date of Patent: Mar. 21, 1989

[54] PRODUCTION OF ORGANIC ACIDS BY AN IMPROVED FERMENTATION PROCESS

[75] Inventors: Phillip J. Brumm; Rathin Datta, Both of Chicago, Ill.

[73] Assignee: Michigan Biotechnology Institute, Lansing, Mich.

[21] Appl. No.: 713,936

[22] Filed: Mar. 20, 1985

[51] Int. Cl.[4] .......................... C12P 7/54; C12P 7/52; C12N 11/02; C12R 1/23

[52] U.S. Cl. .................................... 435/140; 435/139; 435/141; 435/177; 435/178; 435/842; 435/854; 435/822; 426/17

[58] Field of Search ..................... 435/140, 172.1, 253, 435/289, 290, 801, 813, 842, 141, 139, 177, 178, 853, 854, 822; 426/17

[56] References Cited

U.S. PATENT DOCUMENTS

| | | | |
|---|---|---|---|
| 1,459,959 | 6/1923 | Sherman et al. | 435/141 |
| 1,913,346 | 6/1933 | Stiles | 435/140 |
| 1,927,813 | 9/1933 | Legg et al. | 435/141 |
| 4,282,323 | 8/1981 | Yates | 435/140 |
| 4,425,432 | 1/1984 | Zeikus et al. | 435/140 |
| 4,506,012 | 3/1985 | Reed | 435/139 |
| 4,513,084 | 4/1985 | Keller et al. | 435/140 |
| 4,676,987 | 6/1987 | Ahern et al. | 426/41 |

OTHER PUBLICATIONS

Balch, W. E. et al., "Acetobacterium, A New Genus of Hydrogen-Oxidizing Carbon-Dioxide Reducing, Anaerobic Bacterium", *Int'l J. Syst. Bact.,* 27(4):355, (1977).

Liu, J. A. P. et al., "Commensalistic Interaction Between *Lactobacillus acidophillus* and *Propionibacterium shermanii*", *Appl. Env. Microbiol.* 44(3):715, (1982).

Fontaine, et al., "A New Type of Glucose Fermentation by Clostridium Thermoaceticum NSP", J. Bacteriology, 43, 701-715 (1942).

Andreesen, et al. "Fermentation of Glucose, Fructose, and Xylose by Clostridium thermoaceticum, Effect of Metals on Growth Yield, Enzymes, and the Synthesis of Acetate from $CO_2$", J. Bacteriology, 114, 743-751 (1973).

*Primary Examiner*—Elizabeth C. Weimar

*Attorney, Agent, or Firm*—Quarles & Brady

[57] ABSTRACT

Acetic, propionic, and butyric acids are produced by a two-step fermentation process. Lactate salts formed in the second fermentation step, a biochemical acidification step, are used as the carbon source in the first fermentation step.

3 Claims, No Drawings

PRODUCTION OF ORGANIC ACIDS BY AN IMPROVED FERMENTATION PROCESS

FIELD OF THE INVENTION

This invention relates to a fermentation method for producing acetic, propionic, and butyric acids. Free acids are obtained as a result of a biochemical acidification step.

BACKGROUND OF THE INVENTION

The production of organic chemicals by microorganisms is well known to those familiar with the fermentation art. Such fermentation reactions frequently produce a variety of products in dilute aqueous solutions. The expense of separating the chemicals from each other and from the large volume of water has been so great that production of chemicals by fermentation has not been able to compete with production of the same chemicals from fossil fuel sources. However, the gradual depletion of petroleum fossil fuel with the resultant increase in prices of petrochemical feedstocks has revived interest in such fermentation reactions which can convert carbohydrates that are renewable raw materials into simple organic chemicals.

Chemicals which can be produced by fermentation reactions include the aliphatic organic acids: acetic acid, propionic acid, and butyric acid. However, the microorganisms which produce these acids are most productive in growth media at or near a neutral pH. When attempts are made to run these fermentations at low pH where free acids are produced, the organisms do not grow well and only very low concentrations of the acids are obtained. As a result, the fermentations are run at a pH which gives mainly the salts of the acids rather than the free acids themselves.

It is very difficult to separate salts of the organic acids from the dilute aqueous fermentation media in which they are produced. Moreover, the free acids are the products of interest to the chemical industry. For this reason, mineral acids are generally added at the end of the fermentation in order to convert the acid salts to the free acids. This acidification produces quantities of inorganic salts as by-products which are of little value. Their disposal also increases the cost of the process.

A two-step fermentation has now been discovered wherein the second step is a biochemical acidification. The free acid is formed in the second step together with a lactate salt which can be used as the carbon source in the first step of the process. Thus, the present method produces the free acids in good yield and high concentration without giving the useless by-products formed in the prior processes.

Furthermore, the two fermentation steps of this new process are both anaerobic fermentations. Since no oxygen is used in these reactions, no substrate is lost due to oxidation. This provides efficient incorporation of the carbon of the starting material into the product acid. Thus, the process incorporates carbon of the starting material into the product and with the same efficiency as a single-step anaerobic fermenttion.

SUMMARY OF THE INVENTION

In accordance with the present invention, there is provided a process for the preparation of an acid selected from the group consisting of acetic acid, propionic acid, and butyric acid. This process comprises the steps of:

(a) fermenting a fermentation medium containing a lactate salt with a microorganism under conditions suitable for converting the lactate salt to a salt of the selected acid., (b) then adding a fermentable carbohydrate to the mixture of Step (a) to give a second fermentation medium;

(c) fermenting the second fermentation medium with a Lactobacillus under conditions suitable for converting the carbohydrate to a lactate salt while converting the salt of the selected acid to the corresponding free acid;

(d) separating the free acid from the mixture of Step (c) to leave a residual fermentation medium containing lactate salt; and (e) recycling the residual fermentation medium containing lactate salt of Step (d) for use in Step (a).

DETAILED DESCRIPTION OF THE INVENTION

The process of this invention involves two fermentation steps for the production of the lower aliphatic acids. In the first step, a lactate salt is fermented by a microorganism which converts the lactate salt to the salt of the desired acid.

When the process is used to prepare acetic acid, any microorganism capable of converting a lactate salt to a salt of acetic acid can be used in the first fermentation step. However, it is preferable to use a microorganism that forms acetic acid as the sole product. *Clostridium thermoaceticum,* hereafter abbreviated *C. thermoaceticum,* is such an organism.

Any strain of *C. thermoaceticum* which ferments a lactate salt can be employed. The type strain, DSM 521, will ferment a mixture of lactate and a fermentable sugar, such as glucose, but it will not ferment lactate alone. A preferred strain of *C. thermoaceticum* is the mutant strain disclosed in U.S. patent application Ser. No. 474,608, filed Mar. 11, 1983. This strain bears the American Type Culture Collection Deposit No. ATCC 39289. It is capable of fermenting lactate as the only carbon source and can be adapted to grow on a medium having a lactate concentration as high as 0.4 M.

If the process of this invention is used to make propionic or butyric acids, other microorganisms are used to carry out the first fermentation step. If the desired acid is propionic acid, a microorganism is used which converts a lactate salt to a salt of propionic acid. Suitable microorganisms for this purpose include *Propionibacterium freudenreichii,* hereafter abbreviated *P. freudenreichii,* and *Propionibacterium acidi-propionici,* hereafter abbreviated *P. acidi-propionici.* It should be noted that such microorganisms convert a portion of the lactate salt to a salt of acetic acid. However, the principal product of the fermentation is a salt of propionic acid which can be readily separated from the acetic acid in a subsequent step of the process.

When it is desired to make a butyric acid by the process of this invention, the microorganism used in the first fermentation step is one which converts a lactate to a salt of butyric acid. A suitable microorganism for this purpose is *Butyribacterium methylotrophicum,* hereafter abbreviated *B. nethylotrophicum.* With this microorganism, some acetate salt is also formed in the fermentation. However, the acetic acid formed from this salt is readily separated from the butyric acid in a subsequent step because of their differences in boiling point and partition coefficients in various extraction solvents.

The second fermentation step of this invention is carried out by means of a Lactobacillus that will convert a carbohydrate to lactic acid. Suitable microorganisms for carrying out this process include *Lactobacillus bulgaricus, Lactobacillus delbrueckii,* and *Lactobacillus confusus.* A preferred microorganism for this step is *Lactobacillus acidophilus,* hereafter abbreviated *L. acidophilus.*

The second fermentation is carried out after the first fermentation is complete. A fermentable carbohydrate is added to this completed fermentation mixture to give a second fermentation medium. The second fermentation medium is then fermented with the Lactobacillus.

Any carbohydrate which is fermented to lactic acid by the Lactobacillus is suitable for use in the second fermentation step. Suitable carbohydrates include: glucose, fructose, sucrose, starch hydrolyzates, and similar materials.

The Lactobacillus used in the second fermentation grows at an acidic pH. The microorganisms used in the first fermentation do not grow under these conditions. For this reason, the second fermentation can be carried out on the first fermentation mixture without removing cells of the microorganism (e.g., *C. thermoaceticum*) used in the first fermentation. This is particularly useful if the second step is carried out in a batch mode.

It is also possible to carry out the second fermentation step in a continuous mode using cells of the Lactobacillus adsorbed on a solid support. If the second fermentation is carried out in a continuous mode, it is preferable to remove the cells of the microorganism used in the first fermentation before the second fermentation is carried out. The cells can be removed by standard procedures, such as filtration or centrifugation.

The second fermentation is run without pH control. As the lactic acid is produced, the pH of the mixture drops and the acid salt formed in the first fermentation step is converted to the free acid. This free acid is either acetic, propionic, or butyric acid, depending on the microorganism used for the first fermentation step. The lactic acid is simultaneously converted to the lactate salt.

An important discovery which makes this process possible is that the Lactobacillus used in the second fermentation can grow in the presence of high concentrations of acetate, butyrate, and propionate salts. Furthermore, such growth is accomplished without destroying any of these salts or the acids formed from them.

The free acid is separated from the second fermentation mixture by well-known procedures. These include: solvent extraction, adsorption on a solid adsorbent, and distillation. Before the acid is separated from the fermentation mixture, it may be desirable to remove the cells and cell debris from the fermentation mixture. This can be done by conventional means, such as filtration and centrifugation.

After the acid has been removed from the mixture, the residue which contains the lactate salt and other nutrients is reused to make up the fermentation medium for the first fermentation step. The process, thus, efficiently uses the lactate salt produced in the second fermentation step as the raw material for the first fermentation. The net reaction is the conversion of a fermentable carbohydrate to the desired acid. The only by-products of the process are the spent cells of the microorganisms which make a useful supplement to animal feed.

The following examples illustrate certain embodiments of the present invention. Cell strains bearing ATCC numbers are available from the American Type Culture Collection, Rockville, Md. Unless otherwise stated, all proportions and percentages are provided on the basis of weight.

Acetate, butyrate, propionate, and lactate concentrations were determined using high-performance liquid chromatography (HPLC). A sample of fermentation mixture was centrifuged at about 10,000×g for 10 minutes to pellet the cells. Components of the supernatant were chromatographed by elution with 0.06N $H_2SO_4$ from a cation-exchange resin in the hydrogen form. The eluted components were detected by means of a differential refractometer, plotted on a recorder and quantitated using an electronic integrator. The area underneath the curve which represents concentration of each component was reported as a percentage of the total area. The general procedure is that given in "Analyses of Carbohydrate Mixtures by Liquid Chromatography", *Am. Soc. Brew. Chem. Proc.*, 1973, pp. 43–46. The separations were made on a 1-foot HPX-87 column in the hydrogen form, available from Bio-Rad Laboratories, Richmond, Calif.

EXAMPLE 1

Conversion of Lactate to Acetate by *C. thermoaceticum*

The strain of *C. thermoaceticum* used in this example is available from the American Type Culture Collection, Rockville, Md., as ATCC No. 39289.

Medium preparation and cultivation of samples were carried out using standard anaerobic techniques as described by Hungate, R. E., "A Roll Tube Method for Cultivation of Strict Anaerobes", in *Methods in Microbiology,* edited by J. R. Norris and D. W. Ribbons, Vol. 3B, Academic Press, N.Y., 1969, pp. 117–132, and by Miller and Wolin, *Appl. Microbiol.*, 27, 985 (1974).

The medium used for growth of the organism had the following composition:

GROWTH MEDIUM

| Component | Concentration (g/liter) |
|---|---|
| Yeast Extract | 5.0 |
| Tryptone | 5.0 |
| $(NH_4)_2SO_4$ | 1.0 |
| $MgSO_4.7H_2O$ | 0.25 |
| $K_2HPO_4$ | 7.0 |
| $KH_2PO_4$ | 5.5 |
| $Na_2MoO_4.2H_2O$ | 0.002 |
| $Na_2WO_4.2H_2O$ | 0.003 |
| $ZnCl_2$ | 0.00005 |
| $Na_2SeO_3$ | 0.0002 |
| $NiCl_2.6H_2O$ | 0.00002 |
| Resazurin Indicator | 0.002 |
| Ethylenediaminetetraacetic Acid Disodium Salt Dihydrate | 0.005 |
| $MnCl_2.4H_2O$ | 0.005 |
| $H_3BO_3$ | 0.0001 |
| $AlK(SO_4)_2.12H_2O$ | 0.0001 |
| $CuCl_2.2H_2O$ | 0.00001 |

A solution of the growth medium was brought to boiling under a $CO_2$ sparge. Then 0.5 g of sodium thioglycollate and 10 g of $NaHCO_3$ per liter of medium were added. When the medium was fully reduced as shown by the resazurin indicator, it was sparged with $CO_2$ while cooling. Then 30-ml Bellco anaerobic tubes (Bellco Glass Inc., Vineland, N.J.) were filled with 10 ml of the medium under an atmosphere of $N_2$:$H_2$:$CO_2$ (90:5:5) in an anaerobic glove box, stoppered, crimped, and sterilized. Glucose was prepared as a 50% w/v solution by boiling under $CO_2$ sparge for 30 minutes it was then cooled under $CO_2$ and sterilized. Sufficient glucose solution was added to the medium to give a concentration of 15 g/l.

A culture of *C. thermoaceticum* was grown in Bellco tubes containing the medium for 72 hours at 60° C. A 1.0-ml aliquot of this culture was transferred to 10 ml of the standard medium which contained 1.1% sodium lactate in place of the glucose as a carbon source. The culture was incubated at 60° C. for 7 days and the culture was subsequently transferred every 7 days to a medium containing a similar level of sodium lactate.

Increased lactate tolerance was achieved by inoculating tubes of medium containing 0.4% higher sodium lactate. After three subcultures of 7 days each at the higher lactate level, transfers to media containing progressively higher lactate concentrations were repeated until the culture was adapted to grow on a medium containing 0.4M lactate as the only carbon source.

Fermentations of lactate were carried out under pH control using a BioFlo Model C30 fermentor (New Brunswick Scientific, Edison, N.J.). The medium was the same as that used for growth of the organism except that twice the concentrations of yeast extract and tryptone were used. The medium also contained 0.4M lactate (prepared from DL-lactic acid which had been neutralized with sodium hydroxide) in place of the glucose. When the fermentation was run at pH 6.5, concentrations of acetate reached 40 g/l. When fermentations were run at pH 6.8 or run without pH control (final pH about 6.0), they gave about 20 g/l of acetate.

The parent strain of the microorganism, *C. thermoaceticum* (DSM 521), is available from the Deutsche Sammlung von Mikroorganismen Gottingen, West Germany. This strain would not grow on sodium lactate as the only carbon source. However, it would grow and convert dilute solutions (1-2%) sodium lactate to acetate if the medium also contained similar concentrations of glucose.

EXAMPLE 2

Conversion of Lactate to Propionate by Propionibacteria

The general procedures of Example 1 were followed using *P. freudenreichii,* ATCC No. 6207. The growth medium contained the following constituents on a gram per liter basis: yeast extract-20; tryptone - 20; $K_2HPO_4$ - 5; $MnSO_4$ - 0.01., a nonanionic surfactant (TWEEN 80) - 1.0; lactic acid (88%) - 35. The medium was adjusted to pH 6.8-7.0 with NaOH. When the microorganism was grown at 30° C. on the medium of this concentration, all of the lactate was consumed and there was obtained a mixture of propionate (18.5 g/l) and acetate (7.2 g/l). The fermentation required about 10 days for completion.

The microorganism did not grow well on a medium containing higher concentrations of lactate. A fermentation was run in which the medium originally contained 28 grams of lactate per liter and then an additional 28 grams per liter of lactate was added after 4 days of growth. This fermentation, in which the lactate was added in two parts, consumed 54 g/l of lactate and produced 28 g/l propionate and 12 g/l of acetate.

*P. acidi-propionici,* ATCC No. 4965, showed poor initial growth on the medium containing lactate as its sole carbon source. However, repeated transfers through lactate-containing media caused the organism to adapt to this substrate. When so adapted, it converted lactate to propionate and acetate in a similar fashion to that of *P. freudenreichii.*

EXAMPLE 3

Conversion of Lactate to Butyrate and Acetate by *B. methylothrophicum*

The strain of *B. methylothrophicum* used in this example is available from the American Type Culture Collection, Rockville, Md., as ATCC No. 33266.

Medium preparation and cultivation of samples were carried out under anaerobic conditions as in Example 1. The medium used for growth of the organism contained (per liter): $KH_2PO_4$ - 0.3 g; $NH_4Cl$ - 0.3 g; $MgCl_2.2H_2O$ - 0.2 g; $CaCl_2.2H_2O$ - 0.16 g; $NaHCO_3$ - 4 g; yeast extract (Difco) - 0.5 g; vitamins - biotin, para-aminobenzoic acid and calcium pantothenate - 0.05 mg each; and trace minerals containing ca. 0.01 mg each of Fe, Mn, Ca, Zn, Cr, Mo, Ni, and B added via appropriate soluble salts. The carbon sources for fermentation were added to desired concentrations and the medium was reduced to anaerobic conditions by adding a freshly prepared solution of cysteine-cysteine.HCl (at neutral pH) to a concentration of 1 g/liter. Resazurin, a redox indicator, was used as an indicator for reducing conditions. The medium was sterilized by passing through a 0.2-micron filter and dispensed into presterilized anaerobic serum vials capped with butyl rubber stoppers. The fermentation experiments were run in 100 ml of medium contained in 160-ml serum vials at 37°±1° C.

The *B. methylotrophicum* seed culture was grown for 72 hrs in a medium containing 100 mM methanol and 50 mM acetate as carbon sources. The fermentation of lactate was conducted in a medium containing 3.8 g/l lactate and 1.9 g/l acetate (Experiment 1) and 3.8 g/l lactate with no added acetate (Experiment 2). A 5% v/v inoculum was used. The fermentation was conducted at 37° C. and was monitored by measuring optical density, pH and consumption of carbon sources. The fermentation stopped completely after 64 hours and final samples were take to obtain a material balance. Organic acid concentrations in the fermentation.broth were determined by HPLC.

The results are shown in the table below:

| | Lactate (g/l) | | Acetate (g/l) | | Butyrate (g/l) | |
|---|---|---|---|---|---|---|
| | Start | 64 hr | Start | 64 hr | Start | 64 hr |
| Experiment 1 | 3.8 | 1.4 | 1.9 | 2.3 | 0 | 1.2 |
| Experiment 2 | 3.8 | 0.7 | 0.2 | 1.4 | 0 | 1.1 |

In Experiment 1, 1.2 g of butyrate was produced for each 2.6 g of lactate consumed. In Experiment 2, 1.1 g of butyrate was produced for each 3.1 g of lactate consumed. Thus, the experiments show that lactate is converted to butyrate by fermentation by *B. methylotrophicum.*

EXAMPLE 4

Biochemical Acidification of Solutions Containing Sodium Acetate, Sodium Propionate and Sodium Butyrate A strain of *L. acidophilus,* IAM 3532 Institute of Applied Microbiology, University of Tokyo, Bunkyo-ku, Tokyo, Japan, was grown using the general anaerobic techniques of Example 1. The medium used for growth and maintenance of the strain contained the following ingredients on a grams per liter basis: bacto-protease peptone - 10; beef extract - 10; yeast extract - 5; dextrose - 20; TWEEN 80 - 1; ammonium citrate - 2; sodium acetate - 5; $MgSO_4$ - 0.1; $MnSO_4$ - 0.05; $Na_2HPO_4$ - 2.

In order to test the ability of the microorganism to grow in the presence of salts of organic acids, overnight cultures were grown in a medium which contained no sodium acetate. These cultures were used to inoculate a medium of the following composition on a grams per liter basis: yeast extract - 10; tryptone - 10; TWEEN 80 - 1.1; sodium citrate - 2.3; $MgSO_4$ - 0.1; $MnSO_4$ - 0.1; $Na_2HPO_4$ - 1; glucose - 50; and varying amounts of sodium acetate. The mixture was incubated at 37° C. for 4 days, cells were removed by centrifugation and the clear solution was analyzed by HPLC. Results of the experiments given in Table I show that *L. acidophilus* is capable of growing in acetate solution as concentrated as 1.0M with liberation of 30 g/l of free acetic acid.

TABLE I

ACIDIFICATION OF SODIUM ACETATE BY *L. ACIDOPHILUS*

| Acetate Added (g/100 ml) | Final pH | Final Lactate (g/100 ml) | Final Free Acetic Acid (g/100 ml) |
|---|---|---|---|
| 0 | 3.32 | 1.92 | — |
| 1.11 | 3.78 | 3.39 | 1.00 |
| 1.71 | 3.92 | 3.93 | 1.49 |
| 2.28 | 4.05 | 4.26 | 1.90 |
| 2.85 | 4.13 | 4.50 | 2.30 |
| 3.27 | 4.28 | 4.35 | 2.45 |
| 3.93 | 4.42 | 4.41 | 2.68 |
| 4.50 | 4.50 | 4.35 | 2.89 |
| 5.43 | 4.70 | 4.02 | 2.89 |
| 6.51 | 4.82 | 3.96 | 3.00 |

The experiment was repeated using various concentrations of sodium propionate in place of sodium acetate. The results given in Table II show that *L. acidophilus* gives a maximum free acid production in the presence of 0.7M propionate with the maximum conversion of propionate to free acid giving a concentration of 26 g/l of propionic acid.

TABLE II

ACIDIFICATION OF SODIUM PROPIONATE BY *L. ACIDOPHILUS*

| Propionate Added (g/100 ml) | Final pH | Final Lactate (9/100 ml) | Final Free Propionic Acid (g/100 ml) |
|---|---|---|---|
| 0 | 3.40 | 2.00 | — |
| 1.52 | 4.20 | 2.40 | 1.19 |
| 2.48 | 4.40 | 2.80 | 1.72 |
| 4.56 | 4.64 | 3.68 | 2.56 |
| 5.48 | 4.80 | 3.20 | 2.60 |
| 7.28 | 5.40 | 1.16 | 1.35 |

The general procedure was repeated using various concentrations of sodium butyrate in place of sodium acetate. The results given in Table III show that *L. acidophilus* gives a maximum free acid production in the presence of 0.4M butyrate with a maximum free butyric acid production of 16 g/l.

TABLE III

ACIDIFICATION OF SODIUM BUTYRATE BY *L. ACIDOPHILUS*

| Butyrate Added (g/100 ml) | Final pH | Final Lactate (g/100 ml) | Final Free Butyric Acid (g/100 ml) |
|---|---|---|---|
| 0 | 3.22 | 2.00 | — |
| 1.76 | 4.30 | 1.80 | 1.24 |
| 3.52 | 4.80 | 1.76 | 1.63 |
| 4.40 | 4.98 | 1.64 | 1.54 |
| 5.28 | 5.25 | 1.52 | 1.50 |
| 6.16 | 5.26 | 1.52 | 1.48 |
| 7.04 | 5.47 | 1.28 | 1.22 |
| 8.8 | 5.20 | 0.84 | 0.84 |

EXAMPLE 5

Continuous Biochemical Acidification of Sodium Acetate and Sodium Propionate A continuous fermentation was carried out using a culture of *L. acidophilus* adsorbed on corncob granules. The medium used was the same as that used for growth of the *L. acidophilus* in Example 4 except that the concentration of sodium acetate was 1M and the concentration of glucose was 70 g/l.

The corncob granules used were 14–20 mesh (U.S. Standard screen size) available from The Anderson's, Maumee, Ohio, as Grit-O'Cobs, Grade 1420. The reactor containing the granules was a jacketed glass column of 150-ml capacity. The temperature of the column was maintained at 40° C.±1 by passing the liquid through the jacket. The corncob granules were thoroughly washed, sterilized and equilibrated with the medium under anaerobic conditions. The bed was inoculated with 50 ml of a subculture of the microorganism which had been grown for 24 hrs. The medium was slowly passed downward through the column at a flow rate of about 9 ml/hr. After 24 hrs, the rate of flow was increased to about 20 ml/hr to give a residence time of approximately 5 hrs in the column. The column was operated successfully in this manner for 600 hrs with the effluent showing a pH of about 5 corresponding to 21 g/l of undissociated acetic acid. Outflow lactate levels were 25–30 g/l indicating a volumetric productivity of at least 5 g/l-hr of lactate.

A continuous acidification by fermentation was also carried out using the basic medium as described above except that the glucose content was 55 g/l, the sodium acetate content was 28 g/l, and the medium also contained 66 g/l of sodium propionate. The pH of the effluent was 5.1 when the residence time in the reactor was maintained between 5 and 6 hrs. This corresponds to approximately 15 g/l of undissociated propionic acid and 6 g/l of undissociated acetic acid. The reactor was run successfully at 37° C. for over 700 hrs.

This example shows that the biochemical acidification process can be carried out as a continuous reaction.

Thus, it is apparent that there has been provided, in accordance with the invention, a process for the preparation of acetic, propionic, and butyric acids that fully satisfies the objects, aims, and advantages set forth above. While the invention has been described in conjunction with specific embodiments thereof, it is evident that many alternatives, modifications, and variations will be apparent to those skilled in the art in light of the foregoing description. Accordingly, it is intended to include all such alternatives, modifications, and variations as set forth within the spirit and scope of the appended claims.

What is claimed is:

1. A process for the preparation of an acid selected from the group consisting of acetic acid, propionic acid, and butyric acid which comprises the steps of:

(a) fermenting a fermentation medium containing a lactate salt wiht a microorganism selected from a microorganism having the identifying properties of *Clostridium thermoaceticum* ATCC No. 39289, *Propionibacterium freudenreichii* ATCC No. 6207 and *Butyribacterium methylotrophicum* ATCC No. 33266 under conditions suitable for converting the lactate salt to an acetate, a propionate or a butyrate, respectively;

(b) then adding a fermentable carbohydrate to the mixture of Step (a) to give a second fermentation medium;

(c) fermenting the second fermentation medium with a *Lactobacillus acidophilus* IAM 3532 under conditions suitable for converting the carbohydrate to a lactate salt while converting the salt of the selected acid to the corresponding free acid;

(d) separating the free acid from the mixture of Step (c) to leave a residual fermentation medium containing lactate salt; and (e) recycling the residual fermentation medium containing lactate salt of Step (d) for use in Step (a).

2. The process of claim 1 wherein the second fermentation is carried out as a continuous process.

3. The process of claim 2 wherein the *Lactobacillus acidophilus* IAM 3532 is immobilized on corncob granules.

* * * * *